(12) United States Patent
Cuberes Altisen et al.

(10) Patent No.: US 7,998,996 B2
(45) Date of Patent: Aug. 16, 2011

(54) SUBSTITUTED PYRAZOLINE COMPOUNDS FOR REDUCING TRIGLYCERIDES IN BLOOD

(75) Inventors: Rosa Cuberes Altisen, E Barcelona (ES); Bonifacio Gutierrez Silva, Barcelona (ES); Jordi Frigola-Constansa, Sant Just Desvern (ES)

(73) Assignee: Laboratorios del Dr. Esteve S.A., Barcelona (ES)

( * ) Notice: Subject to any disclaimer, the term of this patent is extended or adjusted under 35 U.S.C. 154(b) by 703 days.

(21) Appl. No.: 10/589,743

(22) PCT Filed: Feb. 14, 2005

(86) PCT No.: PCT/EP2005/001465
§ 371 (c)(1),
(2), (4) Date: Mar. 31, 2008

(87) PCT Pub. No.: WO2005/077909
PCT Pub. Date: Aug. 25, 2005

(65) Prior Publication Data
US 2008/0207637 A1    Aug. 28, 2008

Related U.S. Application Data

(63) Continuation of application No. 10/804,534, filed on Mar. 19, 2004, now abandoned.

(30) Foreign Application Priority Data

Feb. 17, 2004 (ES) .................................. 200400378
Sep. 16, 2004 (EP) ..................................... 04021974

(51) Int. Cl.
*A61K 31/415* (2006.01)
*C07D 231/06* (2006.01)

(52) U.S. Cl. .................. 514/406; 548/379.1; 548/379.4; 514/403

(58) Field of Classification Search ............... 548/356.1, 548/379.1, 379.4; 514/403, 406
See application file for complete search history.

(56) References Cited

U.S. PATENT DOCUMENTS

| | | | | |
|---|---|---|---|---|
| 5,091,405 | A | * | 2/1992 | Stevenson ...................... 514/403 |
| 5,700,758 | A | * | 12/1997 | Rosch et al. ................... 504/106 |
| 6,353,117 | B1 | * | 3/2002 | Cuberes-Altisent et al. ........................... 548/379.4 |
| 7,504,519 | B2 | * | 3/2009 | Cuberes Altisen et al. ......................... 548/379.1 |

FOREIGN PATENT DOCUMENTS

| | | |
|---|---|---|
| EP | 1384477 A1 | 1/2004 |
| GB | 1209326 A | 10/1970 |
| WO | 8805046 A2 | 7/1988 |

OTHER PUBLICATIONS

Stevenson et al (1989): STN International HCAPLUS database, (Columbus, Ohio), Accession No. 1989:23882.*
International Search Report issued in counterpart International Application No. PCT/EP2005/001465.

* cited by examiner

*Primary Examiner* — Golam M Shameem
(74) *Attorney, Agent, or Firm* — Banner & Witcoff, Ltd.

(57) ABSTRACT

The present invention relates to substituted pyrazoline compounds, methods for their preparation, medicaments comprising these compounds as well as their use for the preparation of a medicament for the treatment of humans and animal.

17 Claims, 1 Drawing Sheet

Fig. 1)
Effects of the compound according to example 0 on the level of triglycerides in the blood plasma of mice ob/ob
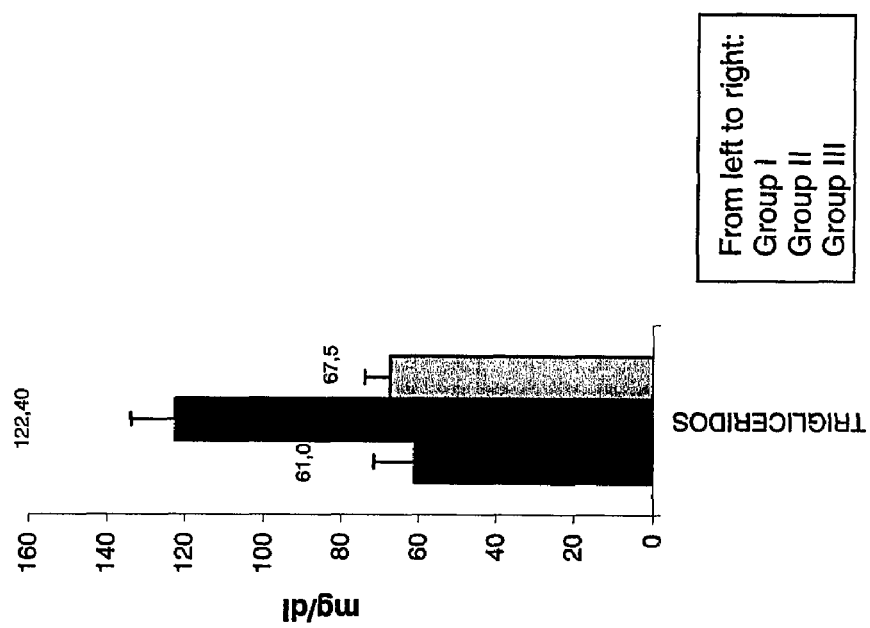

SUBSTITUTED PYRAZOLINE COMPOUNDS FOR REDUCING TRIGLYCERIDES IN BLOOD

The present invention relates to substituted pyrazoline compounds, methods for their preparation, medicaments comprising these compounds as well as their use for the preparation of a medicament for the treatment of humans and animals.

Triglycerides are the chemical form in which most fat exists in food as well as in the body. Triglycerides are present in blood plasma and, in association with cholesterol, form the plasma lipids. Triglycerides in blood plasma are derived from fats consumed directly or are synthesized from e.g. carbohydrates. Superfluous food intake is converted to triglycerides and transported to fat cells to be stored. Elevated triglycerides may also be a consequence of disease states, such as untreated diabetes mellitus. Excess of triglycerides in plasma (hypertriglyceridemia) is linked to the occurrence of coronary artery disease and possibly other disorders.

Therefore, compounds, which have an effect on triglycerides, especially in blood plasma are useful in the prevention and/or treatment of related disorders.

Thus, it was an object of the present invention to provide novel compounds for use as active substances in medicaments, which are suitable for the regulation especially the reduction of triglyceride levels in the blood plasma.

Said object was achieved by providing the substituted pyrazoline compounds of general formula I given below, their stereoisomers, corresponding salts and corresponding solvates thereof.

It has been found that these compounds have a marked effect on the level of triglycerides in the blood plasma.

Thus, in one of its aspects the present invention relates to substituted pyrazoline compounds of general formula

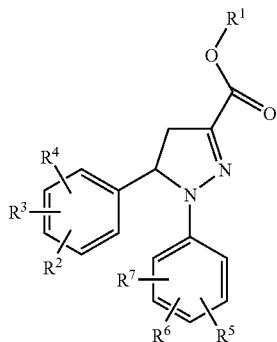

I wherein
R$^1$ represents hydrogen or a linear or branched C$_{1-4}$-alkyl group,
R$^2$, R$^3$ and R$^4$ independently of each other represent hydrogen, a linear or branched C$_{1-6}$-alkyl group, a linear or branched C$_{1-6}$-alkoxy group, a halogen atom, CH$_2$F, CHF$_2$, CF$_3$, CN, OH, NO$_2$, —(C=O)—R$^8$, SH, SR$^8$, SOR$^8$, SO$_2$R$^8$, NH$_2$, NHR$^8$, NR$^8$R$^9$, —(C=O)—NH$_2$, —(C=O)—NHR$^8$ or —(C=O)—NR$^8$R$^9$ whereby R$^8$ and R$^9$ for each substituent independently represent linear or branched C$_{1-6}$ alkyl,
R$^5$ and R$^6$ independently of each other represent a linear or branched C$_{1-6}$-alkyl group, a linear or branched C$_{1-6}$-alkoxy group, a halogen atom, CH$_2$F, CHF$_2$, CF$_3$, CN, OH, NO$_2$, —(C=O)—R$^{10}$, SH, SR$^{10}$, SOR$^{10}$, NH$_2$, NHR$^{10}$, NR$^{10}$R$^{11}$, —(C=O)—NH$_2$, —(C=O)—NHR$^{10}$ and —(C=O)—NR$^{10}$R$^{11}$, whereby R$^{10}$ and optionally R$^{11}$ for each substituent independently represent linear or branched C$_{1-6}$ alkyl;
R$^7$ represents hydrogen, a linear or branched C$_{1-6}$-alkyl group, a linear or branched C$_{1-6}$-alkoxy group, a halogen atom, CH$_2$F, CHF$_2$, CF$_3$, CN, OH, NO$_2$, —(C=O)—R$^{10}$, SH, SR$^{10}$, SOR$^{10}$, NH$_2$, NHR$^{10}$, NR$^{10}$R$^{11}$, —(C=O)—NH$_2$, —(C=O)—NHR$^{10}$ and —(C=O)—NR$^{10}$R$^{11}$, whereby R$^{10}$ and optionally R$^{11}$ for each substituent independently represent linear or branched C$_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

It is very preferred if to these compounds according to formula I the following provisio applies:
with the proviso that
if R$^1$ and R$^7$ are H and R$^5$ and R$^6$ both represent Cl in the 3- and 4-position of the phenyl ring neither of R$^2$, R$^3$ and R$^4$ may represent F in the 4-position of the phenyl ring if the other two of R$^2$, R$^3$ and R$^4$ both represent H.

These compounds had a surprising effect on the blood levels of diet relevant substances, e.g. Triglycerides.

Preferred linear or branched, saturated or unsaturated aliphatic groups, which may be substituted by one or more substituents, may preferably be selected from the group consisting of methyl, ethyl, n-propyl, isopropyl, n-butyl, iso-butyl, sec-butyl, tert-butyl, n-pentyl, n-hexyl, n-heptyl, n-octyl, n-nonyl, n-decyl, vinyl, ethinyl, propenyl, propinyl, butenyl and butinyl.

In the context of this invention, alkyl and cycloalkyl radicals are understood as meaning saturated and unsaturated (but not aromatic), branched, unbranched and cyclic hydrocarbons, which can be unsubstituted or mono- or polysubstituted. In these radicals, C$_{1-2}$-alkyl represents C1- or C2-alkyl, C$_{1-3}$-alkyl represents C1-, C2- or C3-alkyl, C$_{1-4}$-alkyl represents C1-, C2-, C3- or C4-alkyl, C$_{1-5}$-alkyl represents C1-, C2-, C3-, C4-, or C5-alkyl, C$_{1-6}$-alkyl represents C1-, C2-, C3-, C4-, C5- or C6-alkyl, C$_{1-7}$-alkyl represents C1-, C2-, C3-, C4-, C5-, C6- or C7-alkyl, C$_{1-8}$-alkyl represents C1-, C2-, C3-, C4-, C5-, C6-, C7- or C8-alkyl, C$_{1-10}$-alkyl represents C1-, C2-, C3-, C4-, C5-, C6-, C7-, C8-, C9- or C$_{1-10}$-alkyl and C$_{1-18}$-alkyl represents C1-, C2-, C3-, C4-, C5-, C6-, C7-, C8-, C9-, C10-, C11-, C12-, C13-, C14-, C15-, C16-, C17- or C$_{1-8}$-alkyl. Furthermore, C$_{3-4}$-cycloalkyl represents C3- or C4-cycloalkyl, C$_{3-5}$-cycloalkyl represents C3-, C4- or C5-cycloalkyl, C$_{3-6}$-cycloalkyl represents C3-, C4-, C5- or C6-cycloalkyl, C$_{3-7}$-cycloalkyl represents C3-, C4-, C5-, C6- or C7-cycloalkyl, C$_{3-8}$-cycloalkyl represents C3-, C4-, C5-, C6-, C7- or C8-cycloalkyl, C$_{4-5}$-cycloalkyl represents C4- or C5-cycloalkyl, C$_{4-6}$-cycloalkyl represents C4-, C5- or C6-cycloalkyl, C$_{4-7}$-cycloalkyl represents C4-, C5-, C6- or C7-cycloalkyl, C$_{5-6}$-cycloalkyl represents C5- or C6-cycloalkyl and C$_{5-7}$-cycloalkyl represents C5-, C6- or C7-cycloalkyl. In respect of cycloalkyl, the term also includes saturated cycloalkyls in which one or 2 carbon atoms are replaced by a heteroatom, S, N or O. However, mono- or polyunsaturated, preferably monounsaturated, cycloalkyls without a heteroatom in the ring also in particular fall under the term cycloalkyl as long as the cycloalkyl is not an aromatic system. The alkyl and cycloalkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, and also adamantyl, (if substituted also $CHF_2$, $CF_3$ or $CH_2OH$) as well as pyrazolinone, oxopyrazolinone, [1,4]-dioxane or dioxolane.

Here, in connection with alkyl and cycloalkyl—unless expressly defined otherwise—the term substituted in the context of this invention is understood as meaning replacement of at least one hydrogen radical by F, Cl, Br, I, $NH_2$, SH or OH, "polysubstituted" radicals being understood as meaning that the replacement takes effect both on different and on the same atoms several times with the same or different substituents, for example three times on the same C atom, as in the case of $CF_3$, or at different places, as in the case of —CH(OH)—CH=CH—$CHCl_2$. Particularly preferred substituents here are F, Cl and OH. In respect of cycloalkyl, the hydrogen radical can also be replaced by $OC_{1-3}$-alkyl or $C_{1-3}$-alkyl (in each case mono- or polysubstituted or unsubstituted), in particular methyl, ethyl, n-propyl, i-propyl, $CF_3$, methoxy or ethoxy.

The term $(CH_2)_{3-6}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, $(CH_2)_{1-4}$ is to be understood as meaning —$CH_2$—, —$CH_2$—$CH_2$—, —$CH_2$—$CH_2$—$CH_2$— and —$CH_2$—$CH_2$—$CH_2$—$CH_2$—, $(CH_2)_{4-5}$ is to be understood as meaning —$CH_2$—$CH_2$—$CH_2$—$CH_2$— and —$CH_2$—$CH_2$—$CH_2$—$CH_2$—$CH_2$—, etc.

An aryl radical is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or monosubstituted or polysubstituted.

A heteroaryl radical is understood as meaning heterocyclic ring systems which have at least one unsaturated ring and can contain one or more heteroatoms from the group consisting of nitrogen, oxygen and/or sulfur and can also be mono- or polysubstituted. Examples which may be mentioned from the group of heteroaryls are furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole and quinazoline.

Here, in connection with aryl and heteroaryl, substituted is understood as meaning substitution of the aryl or heteroaryl by R, OR, a halogen, preferably F and/or Cl, a $CF_3$, a CN, an $NO_2$, an NRR, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with NH4, but in particular (mono)- or (di)sodium, (mono)- or (di)potassium, magnesium or calcium salts.

These physiologically acceptable salts can also be formed with anions or acids in the context of this invention is understood as meaning salts of at least one of the compounds used according to the invention—usually protonated, for example on the nitrogen—as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The term "solvate" according to this invention is to be understood as meaning any form of the active compound according to the invention in which this compound has attached to it via non-covalent binding another molecule (most likely a polar solvent) especially including hydrates and alcoholates, e.g. methanolate.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or $^{15}N$-enriched nitrogen are within the scope of this invention.

In a preferred embodiment of the invention for a compound according to formula I at least one of $R^2$, $R^3$ or $R^4$ represents hydrogen, while at least one of $R^2$, $R^3$ or $R^4$ is different from hydrogen.

In a preferred embodiment of the invention for a compound according to formula I $R^7$ represents hydrogen.

In a preferred embodiment of the invention for a compound according to formula I $R^2$, $R^3$ and $R^4$ independently of each other represent hydrogen, a linear or branched $C_{1-6}$-alkyl group, a halogen atom, or $CF_3$, preferably $R^2$, $R^3$ and $R^4$ independently of each other represent hydrogen, methyl, ethyl, F, Cl, Br and $CF_3$.

In a preferred embodiment of the invention for a compound according to formula I $R^5$ and $R^6$ independently of each other represent a linear or branched $C_{1-6}$-alkyl group, a halogen atom, or $CF_3$, preferably $R^5$ and $R^6$ independently of each other represent methyl, ethyl, F, Cl, Br and $CF_3$.

In a preferred embodiment of the invention for a compound according to formula I $R^2$ represents a chlorine atom in the 4-position of the phenyl ring, while $R^3$ and $R^4$ represent hydrogen.

In a preferred embodiment of the invention for a compound according to formula I $R^5$ and $R^6$ each represent a chlorine atoms in the 2- and 4-position of the phenyl ring, while $R^7$ represents hydrogen.

In a preferred embodiment of the invention for a compound according to formula I $R^1$ represents hydrogen, methyl or ethyl, preferably hydrogen.

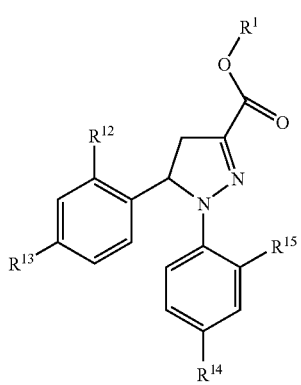

In a highly preferred further aspect of the invention the compound of general formula I is represented by a compound of general formula II
wherein
R$^1$ represents hydrogen or a linear or branched C$_{1-4}$-alkyl group,
R$^{12}$ or R$^{13}$ independently of each other represent a linear or branched C$_{1-6}$-alkyl group, a linear or branched C$_{1-6}$-alkoxy group, a halogen atom, CH$_2$F, CHF$_2$, CF$_3$, CN, OH, NO$_2$, SH, NH$_2$, hydrogen, methyl, ethyl, F, Cl, Br and CF$_3$,
R$^{14}$ or R$^{15}$ independently of each other represent a linear or branched C$_{1-6}$-alkyl group, a linear or branched C$_{1-6}$-alkoxy group, a halogen atom, CH$_2$F, CHF$_2$, CF$_3$, CN, OH, NO$_2$, SH, NH$_2$, methyl, ethyl, F, Cl, Br and CF$_3$,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

In a preferred embodiment of the invention for a compound according to formula II R$^{12}$ and R$^{13}$ independently of each other represent hydrogen, a linear or branched C$_{1-6}$-alkyl group, a halogen atom, or CF$_3$, preferably R$^{12}$ and R$^{13}$ independently of each other represent hydrogen, methyl, ethyl, F, Cl, Br and CF$_3$.

In a preferred embodiment of the invention for a compound according to formula II R$^{14}$, and R$^{15}$ independently of each other represent a linear or branched C$_{1-6}$-alkyl group, a halogen atom, or CF$_3$, preferably R$^{14}$ and R$^{15}$ independently of each other represent methyl, ethyl, F, Cl, Br and CF$_3$.

In a preferred embodiment of the invention for a compound according to formula II R$^{13}$ represents Cl and R$^{12}$ represents hydrogen.

In a preferred embodiment of the invention for a compound according to formula II R$^{14}$ and R$^{15}$ each represent Cl.

In a preferred embodiment of the invention for a compound according to formula II R$^1$ represents hydrogen, methyl or ethyl, preferably hydrogen.

In another preferred embodiment the compound according to formula I or II is selected from the group consisting of:
5-(4-chloro-phenyl)-1-(2,4-dichlorophenyl)-4,5-dihydro-1H-pyrazol-3-carboxylic acid,
optionally in the form of a corresponding N-oxide, a corresponding salt or a corresponding solvate.

Another preferred embodiment of the invention covers also any prodrug of the compounds of the invention described above as well as any medicament comprising this and any use thereof; especially including their esters and ethers. Examples of well known methods of producing a prodrug of a given acting compound are known to those skilled in the art and can be found e.g. in Krogsgaard-Larsen et al., Textbook of Drugdesign and Discovery, Taylor & Francis (April 2002).

Another aspect of the invention is a combination of compounds comprising at least one substituted pyrazoline compound of general formula I

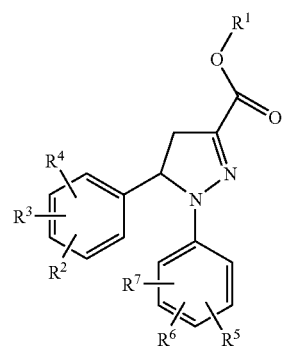

wherein
R$^1$ represents hydrogen or a linear or branched C$_{1-4}$-alkyl group,
R$^2$, R$^3$ and R$^4$ independently of each other represent hydrogen, a linear or branched C$_{1-6}$-alkyl group, a linear or branched C$_{1-6}$-alkoxy group, a halogen atom, CH$_2$F, CHF$_2$, CF$_3$, CN, OH, NO$_2$, —(C=O)—R$^8$, SH, SR$^8$, SOR$^8$, SO$_2$R$^8$, NH$_2$, NHR$^8$, NR$^8$R$^9$, —(C=O)—NH$_2$, —(C=O)—NHR$^3$ or —(C=O)—NR$^8$R$^9$ whereby R$^8$ and R$^9$ for each substituent independently represent linear or branched C$_{1-6}$ alkyl,
R$^5$, R$^6$ and R$^7$ independently of each other represent hydrogen, a linear or branched C$_{1-6}$-alkyl group, a linear or branched C$_{1-6}$-alkoxy group, a halogen atom, CH$_2$F, CHF$_2$, CF$_3$, CN, OH, NO$_2$, —(C=O)—R$^{10}$, SH, SR$^{10}$, SOR$^{10}$, NH$_2$, NHR$^{10}$, NR$^{10}$R$^{11}$, —(C=O)—NH$_2$, —(C=O)—NHR$^{10}$ and —(C=O)—NR$^{10}$R$^{11}$, whereby R$^{10}$ and optionally R$^{11}$ for each substituent independently represent linear or branched C$_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof;
and at least one substituted pyrazoline compound of general formula X

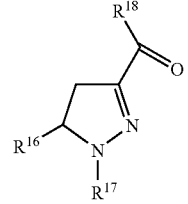

wherein
R$^{16}$ represents an optionally at least mono-substituted phenyl group, $R^{17}$ represents an optionally at least mono-substituted phenyl group, $R^{18}$ represents a saturated or unsaturated, optionally at least mono-substituted, optionally at least one heteroatom as ring member containing cycloaliphatic group, which may be condensed with an optionally at least mono-substituted mono- or polycyclic ring system, or an optionally at least mono-substituted aryl or heteroaryl group, which may be condensed with an optionally at least mono-substituted mono- or polycyclic ring system, or an —$NR^{19}R^{20}$-moiety, $R^{19}$ and $R^{20}$, identical or different, represent a hydrogen atom, an unbranched or branched, saturated or unsaturated, optionally at least mono-substituted aliphatic radical, a saturated or unsaturated, optionally at least mono-substituted, optionally at least one heteroatom as ring member containing cycloaliphatic group, which may be condensed with an optionally at least mono-substituted mono- or polycyclic ring system, or an optionally at least mono-substituted aryl or heteroaryl group, which may be condensed with an optionally at least mono-substituted mono- or polycyclic ring system and/or bonded via a linear or branched alkylene group, an —$SO_2$—$R^{21}$-moiety, or an —$NR^{22}R^{23}$-moiety, with the proviso that $R^{19}$ and $R^{20}$ do not identically represent hydrogen, $R^{21}$ represents a linear or branched, saturated or unsaturated, optionally at least mono-substituted aliphatic group, a saturated or unsaturated, optionally at least mono-substituted, optionally at least one heteroatom as ring member containing cycloaliphatic group, which may be condensed with a mono- or polycyclic ring-system, or an optionally at least mono-substituted aryl or heteroaryl group, which may be condensed with a mono- or polycyclic ring system and/or bonded via a linear or branched alkylene group, $R^{22}$ and $R^{23}$, identical or different, represent a hydrogen atom, an unbranched or branched, saturated or unsaturated, optionally at least mono-substituted aliphatic radical, a saturated or unsaturated, optionally at least mono-substituted, optionally at least one heteroatom as ring member containing cycloaliphatic group, which may be condensed with an optionally at least mono-substituted mono- or polycyclic ring system, or an optionally at least mono-substituted aryl or heteroaryl group, which may be condensed with an optionally at least mono-substituted mono- or polycyclic ring system and/or bonded via a linear or branched alkylene group, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

In a preferred embodiment of the combination of compounds according to the invention for a compound according to formula I at least one of $R^2$, $R^3$ or $R^4$ represents hydrogen, while at least one of $R^2$, $R^3$ or $R^4$ is different from hydrogen.

In a preferred embodiment of the combination of compounds according to the invention for a compound according to formula I at least on of $R^5$, $R^6$ or $R^7$ represents hydrogen, while at least one $R^5$, $R^6$ or $R^7$ is different from hydrogen.

In a preferred embodiment of the combination of compounds according to the invention for a compound according to formula I $R^2$, $R^3$ and $R^4$ independently of each other represent hydrogen, a linear or branched $C_{1-6}$-alkyl group, a halogen atom, or $CF_3$, preferably $R^2$, $R^3$ and $R^4$ independently of each other represent hydrogen, methyl, ethyl, F, Cl, Br and $CF_3$.

In a preferred embodiment of the combination of compounds according to the invention for a compound according to formula I $R^5$, $R^6$ and $R^7$ independently of each other represent hydrogen, a linear or branched $C_{1-6}$-alkyl group, a halogen atom, or $CF_3$, preferably $R^5$, $R^6$ and $R^7$ independently of each other represent hydrogen, methyl, ethyl, F, Cl, Br and $CF_3$.

In a preferred embodiment of the combination of compounds according to the invention for a compound according to formula I $R^2$ represents a chlorine atom in the 4-position of the phenyl ring, while $R^3$ and $R^4$ represent hydrogen.

In a preferred embodiment of the combination of compounds according to the invention for a compound according to formula I $R^5$ and $R^6$ each represent a chlorine atom in the 2- and 4-position of the phenyl ring, while $R^7$ represents hydrogen.

In a preferred embodiment of the combination of compounds according to the invention for a compound according to formula I $R^1$ represents hydrogen, methyl or ethyl, preferably hydrogen.

In a preferred embodiment of the combination of compounds according to the invention the compound of general formula I is represented by a compound of general formula II

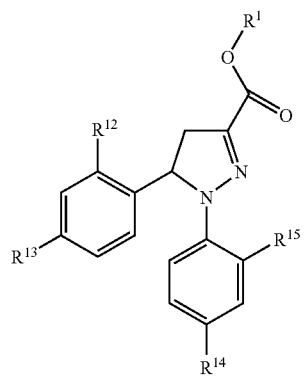

II wherein
$R^1$ represents hydrogen or a linear or branched $C_{1-4}$-alkyl group, $R^{12}$, $R^{13}$, $R^{14}$ or $R^{15}$ independently of each other represent a linear or branched $C_{1-6}$-alkyl group, a linear or branched $C_{1-6}$-alkoxy group, a halogen atom, $CH_2F$, $CHF_2$, $CF_3$, CN, OH, $NO_2$, SH, $NH_2$, hydrogen, methyl, ethyl, F, Cl, Br and $CF_3$, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

In a preferred embodiment of the combination of compounds according to the invention for a compound according to formula II $R^{12}$ and $R^{13}$ independently of each other represent hydrogen, a linear or branched $C_{1-6}$-alkyl group, a halogen atom, or $CF_3$, preferably $R^{12}$ and $R^{13}$ independently of each other represent hydrogen, methyl, ethyl, F, Cl, Br and $CF_3$.

In a preferred embodiment of the combination of compounds according to the invention for a compound according to formula II $R^{14}$, and $R^{15}$ independently of each other represent hydrogen, a linear or branched $C_{1-6}$-alkyl group, a halogen atom, or $CF_3$, preferably $R^{14}$ and $R^{15}$ independently of each other represent hydrogen, methyl, ethyl, F, Cl, Br and $CF_3$.

In a preferred embodiment of the combination of compounds according to the invention for a compound according to formula II $R^{13}$ represents Cl and $R^{12}$ represents hydrogen.

In a preferred embodiment of the combination of compounds according to the invention for a compound according to formula II $R^{14}$ and $R^{15}$ each represent Cl.

In a preferred embodiment of the combination of compounds according to the invention for a compound according to formula II $R^1$ represents hydrogen, methyl or ethyl, preferably hydrogen.

In a preferred embodiment of the combination of compounds according to the invention the compound according to formula I or II is selected from the group consisting of:
5-(4-chloro-phenyl)-1-(2,4-dichlorophenyl)-4,5-dihydro-1H-pyrazol-3-carboxylic acid,
optionally in the form of a corresponding N-oxide, a corresponding salt or a corresponding solvate.

In a preferred embodiment of the combination of compounds according to the invention for a compound according to formula X $R^{16}$ represents a phenyl group, which is optionally substituted by one or more substituents independently selected from the group consisting of a linear or branched $C_{1-6}$-alkyl group, a linear or branched $C_{1-6}$-alkoxy group, a halogen atom, $CH_2F$, $CHF_2$, $CF_3$, CN, OH, $NO_2$, —(C=O)—R', SH, SR', SOR', $SO_2R'$, $NH_2$, NHR', NR'R", —(C=O)—$NH_2$, —(C=O)—NHR' and —(C=O)—NR'R" whereby R' and R" for each substituent independently represent linear or branched $C_{1-6}$ alkyl, preferably $R^{16}$ represents a phenyl group, which is optionally substituted by one or more substituents selected from the group consisting of methyl, ethyl, F, Cl, Br and $CF_3$, more preferably $R^{16}$ represents a phenyl group, which is mono-substituted with a chlorine atom in the 4-position.

In a preferred embodiment of the combination of compounds according to the invention for a compound according to formula X $R^{17}$ represents a phenyl group, which is optionally substituted by one or more substituents independently selected from the group consisting of a linear or branched $C_{1-6}$-alkyl group, a linear or branched $C_{1-6}$-alkoxy group, a halogen atom, $CH_2F$, $CHF_2$, $CF_3$, CN, OH, $NO_2$, —(C=O)—R', SH, SR', SOR', $SO_2R'$, $NH_2$, NHR', NR'R", —(C=O)—$NH_2$, —(C=O)—NHR' and —(C=O)—NR'R", whereby R' and optionally R" for each substituent independently represent linear or branched $C_{1-6}$ alkyl, preferably $R^{17}$ represents a phenyl group, which is optionally substituted by one or more substituents independently selected from the group consisting of methyl, ethyl, F, Cl, Br and $CF_3$, more preferably $R^{17}$ represents a phenyl group, which is di-substituted with two chlorine atoms in its 2- and 4-position.

In a preferred embodiment of the combination of compounds according to the invention for a compound according to formula X $R^{18}$ represents a saturated or unsaturated, optionally at least mono-substituted, optionally at least one heteroatom as ring member containing $C_{3-8}$ cycloaliphatic group, which may be condensed with an optionally at least mono-substituted mono- or polycyclic ring system, or an optionally at least mono-substituted, 5- or 6-membered aryl or heteroaryl group, which may be condensed with an optionally at least mono-substituted mono- or polycyclic ring system, or an —$NR^{19}R^{20}$-moiety, preferably $R^{18}$ represents a saturated, optionally at least mono-substituted, optionally one or more nitrogen-atoms as ring member containing $C_{3-8}$ cycloaliphatic group, which may be condensed with an optionally at least mono-substituted mono- or polycyclic ring system, or an —$NR^{19}R^{20}$-moiety, more preferably $R^{18}$ represents a pyrrolidinyl group, a piperidinyl group or a piperazinyl group, whereby each of these groups may be substituted with one or more $C_{1-6}$-alkyl groups, or an —$NR^{18}R^{19}$-moiety.

In a preferred embodiment of the combination of compounds according to the invention for a compound according to formula X $R^{19}$ and $R^{20}$, identical or different, represent a hydrogen atom, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic group, which may be condensed with an optionally at least mono-substituted mono- or polycyclic ring system, or an optionally at least mono-substituted, 5- or 6-membered aryl or heteroaryl group, which may be condensed with an optionally at least mono-substituted mono- or polycyclic ring system and/or bonded via a methylene (—$CH_2$—) or ethylene (—$CH_2$—$CH_2$)-group, an —$SO_2$—$R^{21}$-moiety, or an —$NR^{22}R^{23}$-moiety, preferably one of these residues $R^{19}$ and $R^{20}$ represents a hydrogen atom and the other one of these residues $R^{19}$ and $R^{20}$ represents a saturated or unsaturated, optionally at least mono-substituted, optionally at least one heteroatom as ring member containing $C_{3-8}$-cycloaliphatic group, which may be condensed with an optionally at least mono-substituted mono- or polycyclic ring system, or an optionally at least mono-substituted, 5- or 6-membered aryl or heteroaryl group, which may be condensed with an optionally at least mono-substituted mono- or polycyclic ring system, an —$SO_2$—$R^{21}$-moiety, or an —$NR^{22}R^{23}$-moiety, or $R^{19}$ and $R^{20}$, identical or different, each represent a $C_{1-6}$ alkyl group, more preferably one of these residues $R^{19}$ and $R^{20}$ represents a hydrogen atom and the other one of these residues $R^{19}$ and $R^{20}$ represents an optionally at least mono-substituted pyrrolidinyl group, an optionally at least mono-substituted piperidinyl group, an optionally at least mono-substituted piperazinyl group, an optionally at least mono-substituted triazolyl group, an —$SO_2$—$R^{21}$-moiety, or an —$NR^{22}R^{23}$-moiety, or $R^{19}$ and $R^{20}$, identical or different, represent a methyl group, an ethyl group, an n-propyl group, an isopropyl group, an n-butyl group, a sec-butyl group or a tert.-butyl group.

In a preferred embodiment of the combination of compounds according to the invention for a compound according to formula X $R^{21}$ represents a linear or branched, saturated or unsaturated, optionally at least mono-substituted $C_{1-6}$ aliphatic group, a saturated or unsaturated, optionally at least mono-substituted, optionally at least one heteroatom as ring member containing $C_{3-8}$ cycloaliphatic group, which may be condensed with a mono- or polycyclic ring-system, or an optionally at least mono-substituted, 5- or 6-membered aryl or heteroaryl group, which may be condensed with a mono- or polycyclic ring system and/or bonded via a methylene (—$CH_2$—) or ethylene (—$CH_2$—$CH_2$)-group, preferably $R^{21}$ represents a $C_{1-6}$-alkyl group, a saturated, optionally at least mono-substituted cycloaliphatic group, which may be condensed with a mono- or polycyclic ring-system, or a phenyl group, which is optionally substituted with one or more $C_{1-6}$ alkyl groups.

In a preferred embodiment of the combination of compounds according to the invention for a compound according to formula X $R^{22}$ and $R^{23}$, identical or different, represent a hydrogen atom, an unbranched or branched, saturated or unsaturated, optionally at least mono-substituted $C_{1-6}$ aliphatic radical, a saturated or unsaturated, optionally at least mono-substituted, optionally at least one heteroatom as ring member containing $C_{3-8}$ cycloaliphatic group, which may be condensed with an optionally at least mono-substituted mono- or polycyclic ring system, or an optionally at least mono-substituted, 5- or 6 membered aryl or heteroaryl group, which may be condensed with an optionally at least mono-substituted mono- or polycyclic ring system and/or bonded via a methylene (—$CH_2$—) or ethylene (—$CH_2$—$CH_2$)-group, preferably $R^{22}$ and $R^{23}$, identical or different, represent a hydrogen atom or a $C_{1-6}$ alkyl radical.

In a preferred embodiment of the combination of compounds according to the invention the compound according to general formula X is represented by a structure wherein $R^{16}$ represents a phenyl ring, which is mono-substituted with a halogen atom, preferably a chlorine atom, in its 4-position, $R^{17}$ represents a phenyl ring, which is di-substituted with two halogen atoms, preferably chlorine atoms, in its 2- and 4-position, $R^{18}$ represents a pyrrolidinyl group, a piperidinyl group, a piperazinyl group, a homo-piperazinyl group, a morpholinyl group, or an —$NR^{19}R^{20}$-moiety, $R^{19}$ represents a hydrogen atom or a linear or branched $C_{1-6}$-alkyl group, $R^{20}$ represents a linear or branched $C_{1-6}$ alkyl group, an —$SO_2$—$R^{21}$-moiety, a pyrrolidinyl group, a piperidinyl group, a piperazinyl group, a homo-piperazinyl group, a morpholinyl group, a triazolyl group, whereby each of the heterocyclic rings may be substituted with one or more, identical or different, $C_{1-6}$-alkyl groups, and $R^{21}$ represents a phenyl group, which is optionally substituted with one or more $C_{1-6}$ alkyl groups, which may be identical or different, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

In a preferred embodiment of the combination of compounds according to the invention the combination of compounds comprises at least one compound according to formula X selected from the group consisting of:

N-piperidinyl-5-(4-chloro-phenyl)-1-(2,4-dichlorophenyl)-4,5-dihydro-1H-pyrazol-3-carboxamide, 5-(4-Chloro-phenyl)-1-(2,4-dichloro-phenyl)-4,5-dihydro-1H-pyrazole-3-carboxylic acid-[1,2,4]-triazole-4-yl-amide, 5-(4-Chloro-phenyl)-1-(2,4-dichloro-phenyl)-4,5-dihydro-1H-pyrazole-3-carboxylic acid-(4-methyl-piperazin-1-yl)-amide, 5-(4-Chloro-phenyl)-1-(2,4-dichloro-phenyl)-4,5-dihydro-1H-pyrazole-3-carboxylic acid diethylamide,

[5-(4-Chloro-phenyl)-1-(2,4-dichloro-phenyl)-4,5-dihydro-1H-pyrazole-3-yl]-piperidine-1-yl-methanone, N-[5-(4-Chloro-phenyl)-1-(2,4-dichlorophenyl)-4,5-dihydro-1H-pyrazole-3-carbonyl]-4-methylphenylsulfonamide, optionally in the form of a corresponding N-oxide, a corresponding salt or a corresponding solvate.

In a preferred embodiment of the combination of compounds according to the invention the combination of compounds comprises at least one compound according to formula X selected from 5-(4-chloro-phenyl)-1-(2,4-dichlorophenyl)-4,5-dihydro-1H-pyrazol-3-carboxylic acid, and
N-piperidinyl-5-(4-chloro-phenyl)-1-(2,4-dichlorophenyl)-4,5-dihydro-1H-pyrazol-3-carboxamide;

each optionally in the form of a corresponding N-oxide, a corresponding salt or a corresponding solvate.

In another aspect the present invention also provides a process for the preparation of substituted pyrazoline compounds of general formula I or II, wherein $R^1$ is hydrogen, given above, in that at least one benzaldehyde compound of general formula III

wherein $R^2$, $R^3$ and $R^4$ have the meaning mentioned above, is reacted with a pyruvate compound of general formula (IV)

wherein G represents an OR group with R being a branched or unbranched $C_{1-6}$ alkyl radical or G represents an O⁻K group with K being a cation, preferably an anorganic kation, more preferably an alkali metal kation, most preferably sodium, to yield a compound of general formula (V)

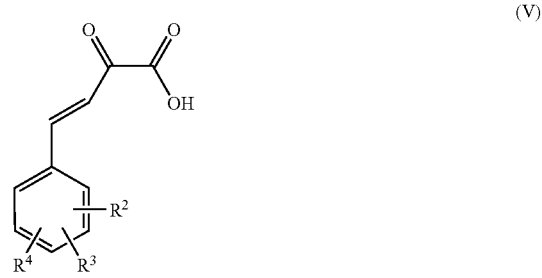

which is optionally isolated and/or optionally purified, and which is reacted with an optionally substituted phenyl hydrazine of general formula (VI)

or a corresponding salt thereof, wherein $R^5$, $R^6$ and $R^7$ have the meaning mentioned above, under inert atmosphere, to yield a compound of general formula (VII)

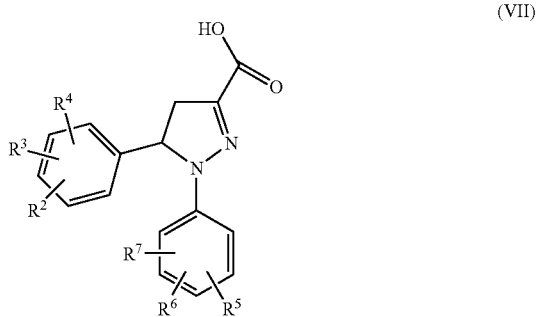

(VII)

wherein $R^2$, $R^3$, $R^4$, $R^5$, $R^6$ and $R^7$ have the meaning as given above, which is optionally isolated and/or optionally purified, and optionally esterified to an alkyl-ester if in the substituted pyrazoline compound of general formula I or II according to the invention $R^1$ is a linear or branched $C_{1-4}$-alkyl group.

The inventive process is also illustrated in scheme I given below:

Scheme I:

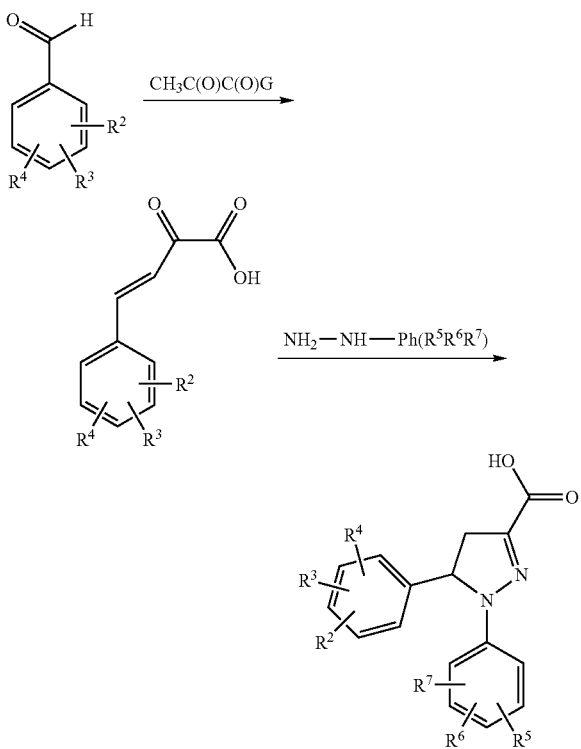

The reaction of the benzaldehyde compound of general formula III with a pyruvate compound of general formula IV is preferably carried out in the presence of at least one base, more preferably in the presence of an alkali metal hydroxide such as sodium hydroxide or potassium hydroxide or an alkali metal methoxide such as sodium methoxide, as described, for example, in Synthetic communications, 26(11), 2229-33, (1996). The respective description is hereby incorporated by reference and forms part of the disclosure. Preferably said reaction is carried out in a protic reaction medium such as a $C_{1-4}$ alkyl alcohol or mixtures of these.

Reaction temperature as well as the duration of the reaction may vary over a broad range. Preferred reaction temperatures range from −10° C. to the boiling point of the reaction medium. Suitable reaction times may vary for example from several minutes to several hours.

Also preferred the reaction of the benzaldehyde compound of general formula III with a pyruvate compound of general formula IV is carried out under acid catalysed conditions, more preferably by refluxing the mixture in dichloromethane in the presence of copper(II) trifluoromethanesulfonate as described, for example, in Synlett, (1), 147-149, 2001. The respective description is hereby incorporated by reference and forms part of the disclosure.

The reaction of the compound of general formula (V) with an optionally substituted phenyl hydrazin of general formula (VI) is preferably carried out in a suitable reaction medium such as $C_{1-4}$-alcohols or ethers such as dioxane or tetrahydrofurane or mixtures of at least two of these afore mentioned compounds. Also preferably, said reaction may be carried out in the presence of an acid, whereby the acid may be organic such as acetic acid and/or inorganic such as hydrochloric acid. Furthermore, the reaction may also be carried out in the presence of a base such as piperidine, piperazine, sodium hydroxide, potassium hydroxide, sodium methoxide or sodium ethoxide, or a mixture of at least two of these bases may also be used.

Reaction temperature as well as the duration of the reaction may vary over a broad range. Suitable reaction temperatures range from room temperature, i.e. approximately 25° C. to the boiling point of the reaction medium. Suitable reaction times may vary for example from several minutes to several hours.

The carboxylic group of the compound of general formula (VII) may be activated for further reactions by the introduction of a suitable leaving group according to conventional methods well known to those skilled in the art. Preferably the compounds of general formula (VII) are transferred into an acid chloride, an acid anhydride, a mixed anhydride, a $C_{1-4}$ alkyl ester, an activated ester such as p-nitrophenylester. Other well known methods for the activation of acids include the activation with N,N-dicyclohexylcarbodiimide or benzotriazol-N-oxotris(dimethylamino) phosphonium hexafluorophosphate (BOP)).

If said activated compound of general formula (VII) is an acid chloride, it is preferably prepared by reaction of the corresponding acid of general formula (VII) with thionyl chloride or oxalyl chloride, whereby said chlorinating agent is also used as the solvent. Also preferably an additional solvent may be used. Suitable solvents include hydrocarbons such as benzene, toluene or xylene, halogenated hydrocarbons such as dichloromethane, chloroform or carbon tetrachloride, ethers such as diethyl ether, dioxane, tetrahydrofurane or dimethoxyethane. Mixtures of two or more solvents from one class or two or more solvents from different classes may also be used. Preferred reaction temperature range from 0° C. to the boiling point of the solvent and reaction times from several minutes to several hours.

If said activated compound of general formula (VII) is a mixed anhydride, said anhydride may preferably be prepared, for example, by reaction of the corresponding acid of general formula (VII) with ethyl chloroformiate in the presence of a base such as triethylamine or pyridine, in a suitable solvent.

Following that the activated compound can be reacted with an alkyl-alcohol to arrive at compounds according to general formulas I or II with $R^1$ being a linear or branched $C_{1-4}$-alkyl group.

During the processes described above the protection of sensitive groups or of reagents may be necessary and/or desirable. The introduction of conventional protective groups as well as their removal may be performed by methods well-known to those skilled in the art.

If the substituted pyrazoline compounds of general formula I or II themselves are obtained in form of a mixture of stereoisomers, particularly enantiomers or diastereomers, said mixtures may be separated by standard procedures known to those skilled in the art, e.g. chromatographic methods or fractionalized crystallization with chiral reagents. It is also possible to obtain pure stereoisomers via stereoselective synthesis.

In a further aspect the present invention also provides a process for the preparation of salts of substituted pyrazoline compounds of general formula I or II and stereoisomers thereof, wherein at least one compound of general formula I or II having at least one basic group is reacted with at least one inorganic and/or organic acid, preferably in the presence of a suitable reaction medium. Suitable reaction media include, for example, any of the ones given above. Suitable inorganic acids include hydrochloric acid, hydrobromic acid, phosphoric acid, sulfuric acid, nitric acid, suitable organic acids are e.g. citric acid, maleic acid, fumaric acid, tartaric acid, or derivatives thereof, p-toluenesulfonic acid, methanesulfonic acid or camphersulfonic acid.

In yet a further aspect the present invention also provides a process for the preparation of salts of substituted pyrazoline compounds of general formula I or II or stereoisomers thereof, wherein at least one compound of general formula I or II having at least one acidic group is reacted with one or more suitable bases, preferably in the presence of a suitable reaction medium. Suitable bases are e.g. hydroxides, carbonates or alkoxides, which include suitable cations, derived e.g. from alkaline metals, alkaline earth metals or organic cations, e.g. $[NH_nR_{4-n}]^+$, wherein n is 0, 1, 2, 3 or 4 and R represents a branched or unbranched $C_{1-4}$-alkyl-radical. Suitable reaction media are, for example, any of the ones given above.

Solvates, preferably hydrates, of the substituted pyrazoline compounds of general formula I or II, of corresponding stereoisomers, of corresponding N-oxides or of corresponding salts thereof may also be obtained by standard procedures known to those skilled in the art.

Substituted pyrazoline compounds of general formula I or II, which comprise nitrogen-atom containing saturated, unsaturated or aromatic rings may also be obtained in the form of their N-oxides by methods well known to those skilled in the art.

The purification and isolation of the inventive substituted pyrazoline compounds of general formula I or II, of a corresponding stereoisomer, or salt, or solvate or any intermediate thereof may, if required, be carried out by conventional methods known to those skilled in the art, e.g. chromatographic methods or recrystallization.

The substituted pyrazoline compounds of general formula I and II given below, their stereoisomers, corresponding N-oxides, corresponding salts thereof and corresponding solvates are toxicologically acceptable and are therefore suitable as pharmaceutical active substances for the preparation of medicaments.

It has been found that the substituted pyrazoline compounds of general formula (I) and (II) given below, stereoisomers thereof, N-oxides thereof, corresponding salts and corresponding solvates have the property to regulate triglyceride levels in blood plasma.

The combination of compounds comprising substituted pyrazoline compounds of general formula (I) and (II) given below, their stereoisomers, corresponding N-oxides, corresponding salts thereof and corresponding solvates and of substituted pyrazoline compounds of general formula (X) given below, their stereoisomers, corresponding N-oxides, corresponding salts thereof and corresponding solvates are toxicologically acceptable and are therefore suitable as pharmaceutical active substances for the preparation of medicaments.

It has been found that the substituted pyrazoline compounds of general formula X given below, stereoisomers thereof, N-oxides thereof, corresponding salts and corresponding solvates have a high affinity to cannabinoid receptors, particularly cannabinoid 1 ($CB_1$)-receptors, i.e. they act as antagonists on these receptors. In particular these pyrazoline compounds show little or no development of tolerance during treatment particularly with respect to food intake. After ending the treatment with the pyrazoline compounds, reduced increase of body weight is found compared to the pre-treatment level.

Thus, another aspect of the present invention relates to a Medicament comprising at least one substituted pyrazoline compound of general formula I or II according to the invention and optionally one or more pharmaceutically acceptable excipients.

Thus, another aspect of the present invention relates to a Medicament comprising at least one substituted pyrazoline compound of general formula I

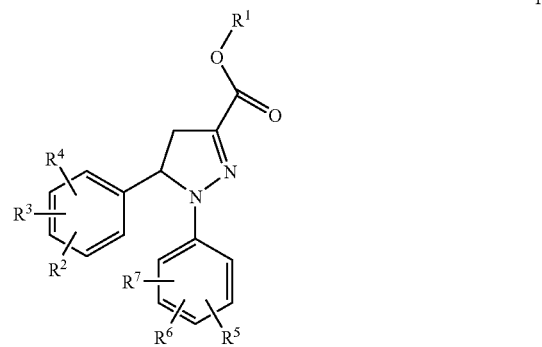

wherein
$R^1$ represents hydrogen or a linear or branched $CO_{14}$-alkyl group,
$R^2$, $R^3$ and $R^4$ independently of each other represent hydrogen, a linear or branched $C_{1-16}$-alkyl group, a linear or branched $C_{1-6}$-alkoxy group, a halogen atom, $CH_2F$, $CHF_2$, $CF_3$, CN, OH, $NO_2$, —(C=O)—$R^8$, SH, $SR^8$, $SOR^8$, $SO_2R'$, $NH_2$, $NHR^8$, $NR^8R^9$, —(C=O)—$NH_2$, —(C=O)—$NHR^8$ or —(C=O)—$NR^8R^9$ whereby $R^8$ and $R^9$ for each substituent independently represent linear or branched $C_{1-6}$ alkyl,
$R^5$, $R^6$ and $R^7$ independently of each other represent hydrogen, a linear or branched $C_{1-6}$-alkyl group, a linear or branched $C_{1-6}$-alkoxy group, a halogen atom, $CH_2F$, $CHF_2$, $CF_3$, CN, OH, $NO_2$, —(C=O)—$R^{10}$, SH, $SR^{10}$, $SOR^{10}$, $NH_2$, $NHR^{10}$, $NR^{10}R^{11}$, —(C=O)—$NH_2$, —(C=O)—$NHR^{10}$ and —(C=O)—$NR^{10}R^{11}$, whereby $R^{10}$ and optionally $R^{11}$ for each substituent independently represent linear or branched $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof;

and optionally one or more pharmaceutically acceptable excipients.

In an embodiment of the medicament according to the invention for the compound according to formula I at least one of $R^2$, $R^3$ or $R^4$ represents hydrogen, while at least one of $R^2$, $R^3$ or $R^4$ is different from hydrogen.

In an embodiment of the medicament according to the invention for the compound according to formula I at least one of $R^5$, $R^6$ or $R^7$ represents hydrogen, while at least one $R^5$, $R^6$ or $R^7$ is different from hydrogen.

In an embodiment of the medicament according to the invention for the compound according to formula I $R^2$, $R^3$ and $R^4$ independently of each other represent hydrogen, a linear or branched $C_{1-6}$-alkyl group, a halogen atom, or $CF_3$, preferably $R^2$, $R^3$ and $R^4$ independently of each other represent hydrogen, methyl, ethyl, F, Cl, Br and $CF_3$.

In an embodiment of the medicament according to the invention for the compound according to formula I $R^5$, $R^6$ and $R^7$ independently of each other represent hydrogen, a linear or branched $C_{1-6}$-alkyl group, a halogen atom, or $CF_3$, preferably $R^5$, $R^6$ and $R^7$ independently of each other represent hydrogen, methyl, ethyl, F, Cl, Br and $CF_3$.

In an embodiment of the medicament according to the invention for the compound according to formula I $R^2$ represents a chlorine atom in the 4-position of the phenyl ring, while $R^3$ and $R^4$ represent hydrogen.

In an embodiment of the medicament according to the invention for the compound according to formula I $R^5$ and $R^6$ each represent a chlorine atoms in the 2- and 4-position of the phenyl ring, while $R^7$ represents hydrogen.

In an embodiment of the medicament according to the invention for the compound according to formula I $R^1$ represents hydrogen, methyl or ethyl, preferably hydrogen.

In an embodiment of the medicament according to the invention the compound according to formula I is represented by a compound of general formula (II)

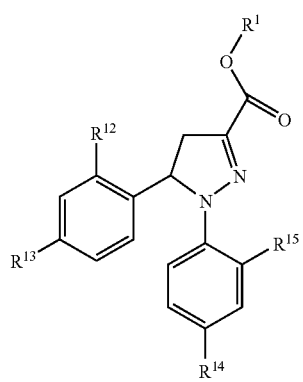

wherein
$R^1$ represents hydrogen or a linear or branched $C_{1-4}$-alkyl group, $R^{12}$, $R^{13}$, $R^{14}$ or $R^{15}$ independently of each other represent a linear or branched $C_{1-6}$-alkyl group, a linear or branched $C_{1-6}$-alkoxy group, a halogen atom, $CH_2F$, $CHF_2$, $CF_3$, CN, OH, $NO_2$, SH, $NH_2$, hydrogen, methyl, ethyl, F, Cl, Br and $CF_3$, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

In an embodiment of the medicament according to the invention for the compound according to formula II $R^{12}$ and $R^{13}$ independently of each other represent hydrogen, a linear or branched $C_{1-6}$-alkyl group, a halogen atom, or $CF_3$, preferably $R^{12}$ and $R^{13}$ independently of each other represent hydrogen, methyl, ethyl, F, Cl, Br and $CF_3$.

In an embodiment of the medicament according to the invention for the compound according to formula II $R^{14}$, and $R^{15}$ independently of each other represent hydrogen, a linear or branched $C_{1-6}$-alkyl group, a halogen atom, or $CF_3$, preferably $R^{14}$ and $R^{15}$ independently of each other represent hydrogen, methyl, ethyl, F, Cl, Br and $CF_3$.

In an embodiment of the medicament according to the invention for the compound according to formula II $R^{13}$ represents Cl and $R^{12}$ represents hydrogen.

In an embodiment of the medicament according to the invention for the compound according to formula II $R^{14}$ and $R^{15}$ each represent Cl.

In an embodiment of the medicament according to the invention for the compound according to formula II $R^1$ represents hydrogen, methyl or ethyl, preferably hydrogen.

In an embodiment of the medicament according to the invention the compound according to formulas I or II is selected from the group consisting of:
5-(4-chloro-phenyl)-1-(2,4-dichlorophenyl)-4,5-dihydro-1H-pyrazol-3-carboxylic acid,
optionally in the form of a corresponding N-oxide, a corresponding salt or a corresponding solvate.

Another aspect of the invention is a medicament comprising at least one combination of compounds according to the invention and optionally one or more pharmaceutically acceptable excipients.

In an embodiment of the medicaments according to the invention the medicament is for the regulation of triglyceride levels in the blood plasma and for the prophylaxis and/or treatment of disorders of the central nervous system, especially stroke, of disorders of the cardiovascular system and of food intake disorders, preferably bulimia, anorexia, cachexia, obesity, type II diabetus mellitus (non-insulin dependent diabetes mellitus), preferably obesity and diabetes.

In an embodiment of the medicament comprising the compound according to formula I or II according to the invention the medicament is for the prophylaxis and/or treatment of disorders of the central nervous system, disorders of the immune system, disorders of the cardiovascular system, disorders of the endocrinous system, disorders of the respiratory system, disorders of the gastrointestinal tract or reproductive disorders.

In an embodiment of the medicament comprising the combination according to the invention the medicament is for the modulation of cannabinoid-receptors, preferably cannabinoid 1 ($CB_1$) receptors, for the prophylaxis and/or treatment of disorders of the central nervous system, disorders of the immune system, disorders of the cardiovascular system, disorders of the endocrinous system, disorders of the respiratory system, disorders of the gastrointestinal tract or reproductive disorders.

In an embodiment of the medicaments according to the invention the medicament is for the prophylaxis and/or treatment of food intake disorders, preferably bulimia, anorexia, cachexia, obesity, type II diabetus mellitus (non-insulin dependent diabetes mellitus), preferably obesity.

In an embodiment of the medicaments according to the invention the medicament is for the prophylaxis and/or treatment of psychosis.

In an embodiment of the medicaments according to the invention the medicament is for the prophylaxis and/or treatment of alcohol abuse and/or addiction, nicotine abuse and/or addiction, drug abuse and/or addiction and/or medicament abuse and/or addiction, preferably drug abuse and/or addiction and/or nicotine abuse and/or addiction.

In an embodiment of the medicaments according to the invention the medicament is for the prophylaxis and/or treatment of one or more disorders selected from the group consisting of schizophrenia, anxiety, depression, epilepsy, neurodegenerative disorders, cerebellar disorders, spinocerebellar disorders, cognitive disorders, cranial trauma, panic attacks, peripheric neuropathy, glaucoma, migraine, Morbus Parkinson, Morbus Huntington, Morbus Alzheimer, Raynaud's disease, tremblement disorders, compulsive disorders, senile dementia, thymic disorders, tardive dyskinesia, bipolar disorders; bone disorders including osteoporosis or Paget's disease of bone; cancer, preferably for the prophylaxis and/or treatment of one or more types of cancer selected from the group consisting of brain cancer, bone cancer, lip cancer, mouth cancer, esophageal cancer, stomach cancer, liver cancer, bladder cancer, pancreas cancer, ovary cancer, cervical cancer, lung cancer, breast cancer, skin cancer, colon cancer, bowl cancer and prostate cancer, more preferably for the prophylaxis and/or treatment of one or more types of cancer selected from the group consisting of colon cancer, bowel cancer and prostate cancer; medicament-induced movement disorders, dystonia, endotoxemic shock, hemorragic shock, hypotension, insomnia, immunologic disorders, sclerotic plaques, vomiting, diarrhea, asthma, memory disorders, pruritus, pain, or for potentiation of the analgesic effect of narcotic and non-narcotic analgesics, or for influencing intestinal transit.

Said medicaments may also comprise any combination of one or more of the substituted pyrazoline compounds of general formula I given above, stereoisomers thereof, corresponding N-oxides thereof, physiologically acceptable salts thereof or physiologically acceptable solvates thereof.

Particularly preferably said medicaments are suitable for the prophylaxis and/or treatment of alcohol abuse, drug abuse and/or medicament abuse, preferably drug abuse and the treatment of obesity.

Medicaments and/or drugs, which are frequently the subject of misuse include opioids, barbiturates, cannabis, cocaine, amphetamines, phencyclidine, hallucinogens and benzodiazepines.

The medicament according to the present invention may be in any form suitable for the application to humans and/or animals, preferably humans including infants, children and adults and can be produced by standard procedures known to those skilled in the art. The composition of the medicament may vary depending on the route of administration.

The medicament of the present invention may for example be administered parentally in combination with conventional injectable liquid carriers, such as water or suitable alcohols. Conventional pharmaceutical excipients for injection, such as stabilizing agents, solubilizing agents, and buffers, may be included in such injectable compositions. These medicaments may for example be injected intramuscularly, intraperitoneally, or intravenously.

Solid oral compositions (which are preferred as are liquid ones) may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to the methods well known in normal pharmaceutical practice, in particular with an enteric coating.

The mentioned formulations will be prepared using standard methods such as those described or referred to in the Spanish and US Pharmacopeias and similar reference texts.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, capsules, lozenges, aqueous or oily solutions, suspensions, emulsions, or dry powdered forms suitable for reconstitution with water or other suitable liquid medium before use, for immediate or retarded release.

The liquid oral forms for administration may also contain certain additives such as sweeteners, flavoring, preservatives, and emulsifying agents. Non-aqueous liquid compositions for oral administration may also be formulated, containing edible oils.

Such liquid compositions may be conveniently encapsulated in e.g., gelatin capsules in a unit dosage amount.

The compositions of the present invention may also be administered topically or via a suppository.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

Another preferred aspect of the invention is the use of at least one substituted pyrazoline compound of formula I or II according to the invention or at least one combination of compounds according to the invention (and optionally one or more pharmaceutically acceptable excipients), for the preparation of a medicament for the regulation of triglyceride levels in the blood plasma and for the prophylaxis and/or treatment of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

Another preferred aspect of the invention is the use of at least one substituted pyrazoline compound of formula I or II according to the invention (and optionally one or more pharmaceutically acceptable excipients,) for the preparation of a medicament for the prophylaxis and/or treatment of disorders of the central nervous system, disorders of the immune system, disorders of the cardiovascular system, disorders of the endocrinous system, disorders of the respiratory system, disorders of the gastrointestinal tract or reproductive disorders.

Another preferred aspect of the invention is the use of at least one combination of compounds according to the invention (and optionally one or more pharmaceutically acceptable excipients,) for the preparation of a medicament for the modulation of cannabinoid-receptors, preferably cannabinoid 1 ($CB_1$) receptors, for the prophylaxis and/or treatment of disorders of the central nervous system, disorders of the immune system, disorders of the cardiovascular system, disorders of the endocrinous system, disorders of the respiratory system, disorders of the gastrointestinal tract or reproductive disorders.

Another preferred aspect of the invention is the use of at least one substituted pyrazoline compound of formula I or II according to the invention or at least one combination of compounds according to the invention (and optionally one or more pharmaceutically acceptable excipients), for the preparation of a medicament for the prophylaxis and/or treatment of food intake disorders, preferably bulimia, anorexia, cachexia, obesity, type II diabetus mellitus (non-insulin dependent diabetes mellitus), preferably obesity.

Another preferred aspect of the invention is the use of at least one substituted pyrazoline compound of formula I or II according to the invention or at least one combination of compounds according to the invention (and optionally one or more pharmaceutically acceptable excipients), for the preparation of a medicament for the prophylaxis and/or treatment of psychosis.

Another preferred aspect of the invention is the use of at least one substituted pyrazoline compound of formula I or II according to the invention or at least one combination of compounds according to the invention (and optionally one or more pharmaceutically acceptable excipients), for the preparation of a medicament for the prophylaxis and/or treatment of alcohol abuse and/or addiction, nicotine abuse and/or addiction, medicament abuse and/or addiction and/or drug abuse and/or addiction, preferably drug abuse and/or addiction or nicotine abuse and/or addiction.

Another preferred aspect of the invention is the use of at least one substituted pyrazoline compound of formula I or II according to the invention or at least one combination of compounds according to the invention (and optionally one or more pharmaceutically acceptable excipients), for the preparation of a medicament for the prophylaxis and/or treatment of one or more disorders selected from the group consisting of schizophrenia, anxiety, depression, epilepsy, neurodegenerative disorders, cerebellar disorders, spinocerebellar disorders, cognitive disorders, cranial trauma, panic attacks, peripheric neuropathy, glaucoma, migraine, Morbus Parkinson, Morbus Huntington, Morbus Alzheimer, Raynaud's disease, tremblement disorders, compulsive disorders, senile dementia, thymic disorders, tardive dyskinesia, bipolar disorders; bone disorders including osteoporosis or Paget's disease of bone; cancer, preferably for the prophylaxis and/or treatment of one or more types of cancer selected from the group consisting of brain cancer, bone cancer, lip cancer, mouth cancer, esophageal cancer, stomach cancer, liver cancer, bladder cancer, pancreas cancer, ovary cancer, cervical cancer, lung cancer, breast cancer, skin cancer, colon cancer, bowl cancer and prostate cancer, more preferably for the prophylaxis and/or treatment of one or more types of cancer selected from the group consisting of colon cancer, bowel cancer and prostate cancer; medicament-induced movement disorders, dystonia, endotoxemic shock, hemorragic shock, hypotension, insomnia, immunologic disorders, sclerotic plaques, vomiting, diarrhea, asthma, memory disorders, pruritus, pain, or for potentiation of the analgesic effect of narcotic and non-narcotic analgesics, or for influencing intestinal transit.

Another preferred aspect of the invention is the use of at least one substituted pyrazoline compound of general formula I

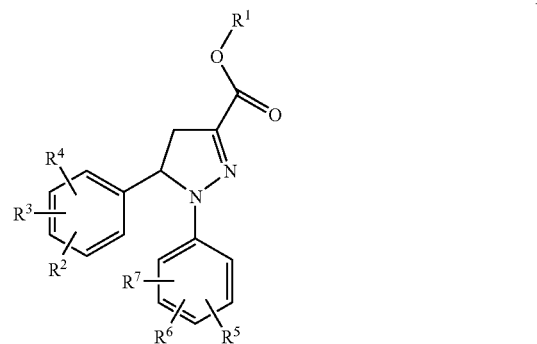

wherein
$R^1$ represents hydrogen or a linear or branched $C_{1-4}$-alkyl group,
$R^2$, $R^3$ and $R^4$ independently of each other represent hydrogen, a linear or branched $C_{1-6}$-alkyl group, a linear or branched $C_{1-6}$-alkoxy group, a halogen atom, $CH_2F$, $CHF_2$, $CF_3$, CN, OH, $NO_2$, —(C=O)—$R^8$, SH, $SR^8$, $SOR^8$, $SO_2R^8$, $NH_2$, $NHR^8$, $NR^8R^9$, —(C=O)—$NH_2$, —(C=O)—$NHR^8$ or —(C=O)—$NR^8R^9$ whereby $R^8$ and $R^9$ for each substituent independently represent linear or branched $C_{1-6}$ alkyl,
$R^5$, $R^6$ and $R^7$ independently of each other represent hydrogen, a linear or branched $C_{1-6}$-alkyl group, a linear or branched $C_{1-6}$-alkoxy group, a halogen atom, $CH_2F$, $CHF_2$, $CF_3$, CN, OH, $NO_2$, —(C=O)—$R^{10}$, SH, $SR^{10}$, $SOR^{10}$, $NH_2$, $NHR^{10}$, $NR^{10}R^{11}$, —(C=O)—$NH_2$, —(C=O)—$NHR^{10}$ and —(C=O)—$NR^{10}R^{11}$, whereby $R^{10}$ and optionally $R^{11}$ for each substituent independently represent linear or branched $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof;
and optionally one or more pharmaceutically acceptable excipients, for the preparation of a medicament for the regulation of triglyceride levels in the blood plasma and for the prophylaxis and/or treatment of disorders of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

Another preferred aspect of the invention is the use for the manufacture of a medicament of at least one substituted pyrazoline compound of formula I for which at least one of $R^2$, $R^3$ or $R^4$ represents hydrogen, while at least one of $R^2$, $R^3$ or $R^4$ is different from hydrogen for the manufacture of a medicament for the regulation of triglyceride levels in the blood plasma and for the prophylaxis and/or treatment of disorders of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

Another preferred aspect of the invention is the use of at least one substituted pyrazoline compound of formula I for which at least on of $R^5$, $R^6$ or $R^7$ represents hydrogen, while at least one $R^5$, $R^6$ or $R^7$ is different from hydrogen for the manufacture of a medicament for the regulation of triglyceride levels in the blood plasma and for the prophylaxis and/or treatment of disorders of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

Another preferred aspect of the invention is the use of at least one substituted pyrazoline compound of formula I for which $R^2$, $R^3$ and $R^4$ independently of each other represent hydrogen, a linear or branched $C_{1-6}$-alkyl group, a halogen atom, or $CF_3$, preferably $R^2$, $R^3$ and $R^4$ independently of each other represent hydrogen, methyl, ethyl, F, Cl, Br and $CF_3$ for the manufacture of a medicament for the regulation of triglyceride levels in the blood plasma and for the prophylaxis and/or treatment of disorders of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

Another preferred aspect of the invention is the use of at least one substituted pyrazoline compound of formula I for which $R^5$, $R^6$ and $R^7$ independently of each other represent hydrogen, a linear or branched $C_{1-6}$-alkyl group, a halogen atom, or $CF_3$, preferably $R^5$, $R^6$ and $R^7$ independently of each other represent hydrogen, methyl, ethyl, F, Cl, Br and $CF_3$ for the manufacture of a medicament for the regulation of triglyceride levels in the blood plasma and for the prophylaxis and/or treatment of disorders of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

Another preferred aspect of the invention is the use of at least one substituted pyrazoline compound of formula I for which $R^2$ represents a chlorine atom in the 4-position of the phenyl ring, while $R^3$ and $R^4$ represent hydrogen for the manufacture of a medicament for the regulation of triglyceride levels in the blood plasma and for the prophylaxis and/or treatment of disorders of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

Another preferred aspect of the invention is the use of at least one substituted pyrazoline compound of formula I for which $R^5$ and $R^6$ each represent a chlorine atoms in the 2- and 4-position of the phenyl ring, while $R^7$ represents hydrogen for the manufacture of a medicament for the regulation of triglyceride levels in the blood plasma and for the prophylaxis and/or treatment of disorders of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

Another preferred aspect of the invention is the use of at least one substituted pyrazoline compound of formula I for which $R^1$ represents hydrogen, methyl or ethyl, preferably hydrogen for the manufacture of a medicament for the regulation of triglyceride levels in the blood plasma and for the prophylaxis and/or treatment of disorders of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

Another preferred aspect of the invention is the use of at least one substituted pyrazoline compound of formula wherein the compound of general formula (I) is represented by a compound of general formula (II)

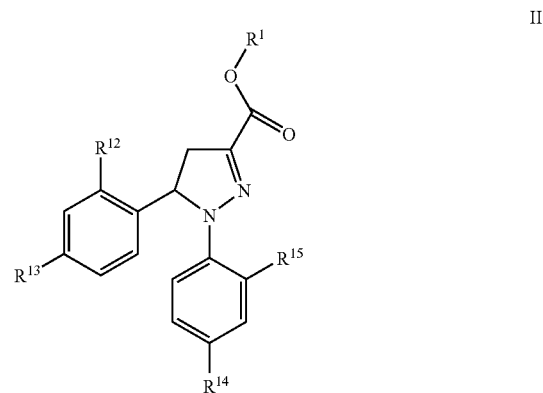

wherein
$R^1$ represents hydrogen or a linear or branched $C_{1-4}$-alkyl group,
$R^{12}$, $R^{13}$, $R^{14}$ or $R^{15}$ independently of each other represent a linear or branched $C_{1-6}$-alkyl group, a linear or branched $C_{1-6}$-alkoxy group, a halogen atom, $CH_2F$, $CHF_2$, $CF_3$, CN, OH, $NO_2$, SH, $NH_2$, hydrogen, methyl, ethyl, F, Cl, Br and $CF_3$,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof
for the manufacture of a medicament for the regulation of triglyceride levels in the blood plasma and for the prophylaxis and/or treatment of disorders of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

Another embodiment of the invention is the use of at least one substituted pyrazoline compound of formula II for which $R^{12}$ and $R^{13}$ independently of each other represent hydrogen, a linear or branched $C_{1-6}$-alkyl group, a halogen atom, or $CF_3$, preferably $R^{12}$ and $R^{13}$ independently of each other represent hydrogen, methyl, ethyl, F, Cl, Br and $CF_3$ for the manufacture of a medicament for the regulation of triglyceride levels in the blood plasma and for the prophylaxis and/or treatment of disorders of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

Another embodiment of the invention is the use of at least one substituted pyrazoline compound of formula II for which $R^{14}$, and $R^{15}$ independently of each other represent hydrogen, a linear or branched $C_{1-6}$-alkyl group, a halogen atom, or $CF_3$, preferably $R^{14}$ and $R^{15}$ independently of each other represent hydrogen, methyl, ethyl, F, Cl, Br and $CF_3$ for the manufacture of a medicament for the regulation of triglyceride levels in the blood plasma and for the prophylaxis and/or treatment of disorders of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

Another embodiment of the invention is the use of at least one substituted pyrazoline compound of formula II for which $R^{13}$ represents Cl and $R^{12}$ represents hydrogen for the manufacture of a medicament for the regulation of triglyceride levels in the blood plasma and for the prophylaxis and/or treatment of disorders of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

Another preferred embodiment of the invention is the use of at least one substituted pyrazoline compound of formula II for which $R^{14}$ and $R^{15}$ each represent Cl for the manufacture of a medicament for the regulation of triglyceride levels in the blood plasma and for the prophylaxis and/or treatment of disorders of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

Another preferred embodiment of the invention is the use of at least one substituted pyrazoline compound of formula II for which $R^1$ represents hydrogen, methyl or ethyl, preferably hydrogen for the manufacture of a medicament for the regulation of triglyceride levels in the blood plasma and for the prophylaxis and/or treatment of disorders of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

Another embodiment of the invention is the use of at least one substituted pyrazoline compound of formula I or II for which the compound according to formulas I or II is selected from the group consisting of:
5-(4-chloro-phenyl)-1-(2,4-dichlorophenyl)-4,5-dihydro-1H-pyrazol-3-carboxylic acid,
optionally in the form of a corresponding N-oxide, a corresponding salt or a corresponding solvate;
for the manufacture of a medicament for the regulation of triglyceride levels in the blood plasma and for the prophylaxis and/or treatment of disorders of disorders of the central nervous system, especially stroke, of disorders of the cardiovascular system and of food intake disorders, especially bulimia, anorexia, cachexia, obesity, type II diabetus mellitus (non-insulin dependent diabetes mellitus), preferably obesity and diabetes.

The present invention is illustrated below with the aid of examples. These illustrations are given solely by way of example and are not intended to limit the present invention.

EXAMPLES

Example 0 represent a compound according to formula I or II.

Example 0

5-(4-chlorophenyl)-1-(2,4-dichlorophenyl)-4,5-dihydro-pyrazole-3-carboxylic acid a) 4-(4-chlorophenyl)-2-oxo-3-butenoic acid

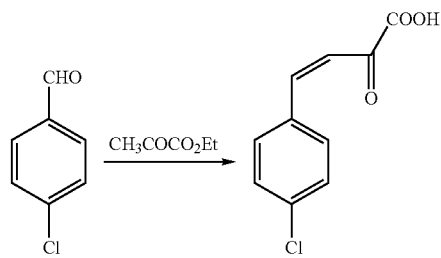

In a three neck flask p-chlorobenzaldehyde (13.3 g, 95 mmoles) and ethyl pyruvate (10 g, 86 mmoles) were dissolved in 150 ml of absolute ethanol. The solution was ice-cooled to 0° C. and an aqueous solution of NaOH (3.8 g in 45 mL water) was added dropwise keeping the temperature below or equal to 10° C., whereby a yellow-orange colored precipitate was formed. The reaction mixture was stirred for 1 hour at 0° C. and an additional 1.5 hours at room temperature (approximately 25° C.). Afterwards the reaction mixture was cooled down to approximately 5° C. and the insoluble sodium salt of 4-(4-chlorophenyl)-2-oxo-3-butenoic acid was isolated by filtration.

The filtrate was left in the refrigerator overnight, whereby more precipitate is formed, which was filtered off, combined with the first fraction of the salt and washed with diethyl ether. The sodium salt of 4-(4-chlorophenyl)-2-oxo-3-butenoic acid was then treated with a solution of 2N HCl, stirred for some minutes and solid 4-(4-chlorophenyl)-2-oxo-3-butenoic acid was separated via filtration and dried to give 12.7 g of the desired product (70% of theoretical yield).

IR (KBr, $cm^{-1}$): 3500-2500, 1719.3, 1686.5, 1603.4, 1587.8, 1081.9.
$^1$H NMR (CDCl$_3$, δ): 7.4 (d, J=8.4 Hz, 2H), 7.5 (d, J=16.1 Hz, 1H), 7.6 (d, J=8.4 Hz, 2H), 8.1 (d, J=16.1 Hz, 1H).

a2) 5-(4-chlorophenyl)-1-(2,4-dichlorophenyl)-4,5-dihydro-pyrazole-3-carboxylic acid In an alternative route instead of using ethylpyruvate the salt $CH_3$—C(O)—C(O)—O$^-$ Na$^+$ (sodiumpyruvate) was used, dissolved ethanolic water.

b) 5-(4-chlorophenyl)-1-(2,4-dichlorophenyl)-4,5-dihydro-pyrazole-3-carboxylic acid

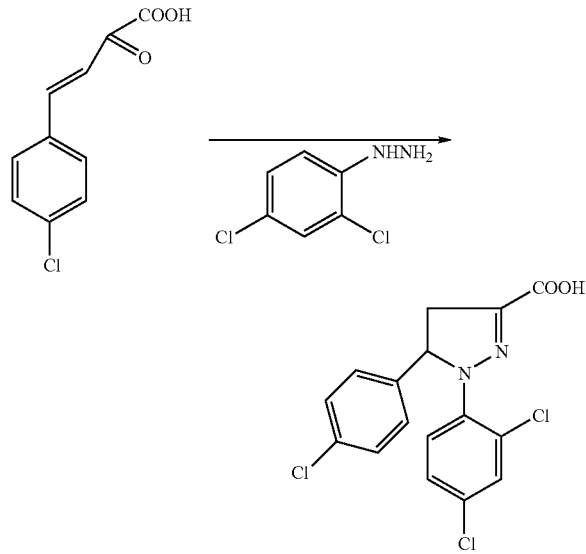

4-(4-chlorophenyl)-2-oxo-3-butenoic acid obtained according to step a) (12.6 g, 60 mmoles), 2,4-dichlorophenylhydrazine hydrochloride (12.8 g, 60 mmoles) and glacial acetic acid (200 mL) were mixed under a nitrogen atmosphere and heated to reflux for 4 hours, cooled down to room temperature (approximately 25° C.) and given into ice-water, whereby a sticky mass was obtained, which was extracted with methylene chloride. The combined methylene chloride fractions were washed with water, dried with sodium sulfate, filtered and evaporated to dryness to give a pale yellow solid (12.7 g, 57% of theoretical yield).

IR (KBr, cm$^{-1}$): 3200-2200, 1668.4, 1458, 1251.4, 1104.8.
$^1$H NMR (CDCl$_3$, δ): 3.3 (dd, 1H), 3.7 (dd, 1H), 5.9 (dd, 1H), 7.09-7.25 (m, 7H).

The Examples 1 to 6 represent compounds according to formula X.

Example 1

N-piperidinyl-5-(4-chlorophenyl)-1-(2,4-dichlorophenyl)-4,5-dihydro-1H-pyrazole-3-carboxamide

(a) 5-(4-chlorophenyl)-1-(2,4-dichlorophenyl)-4,5-dihydro-pyrazole-3-carboxylic acid chloride

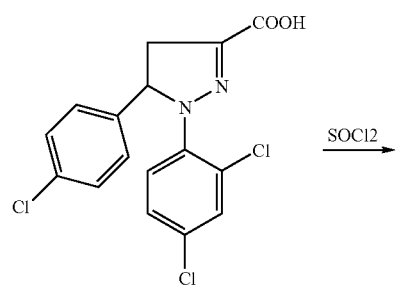

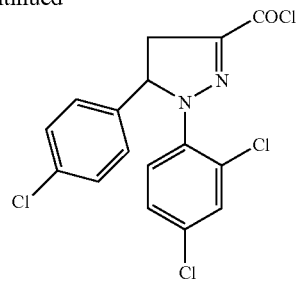

Under nitrogen atmosphere 5-(4-chlorophenyl)-1-(2,4-dichlorophenyl)-4,5-dihydro-pyrazole-3-carboxylic acid (2.5 g, 6.8 mmols) obtained according to Example 0 was dissolved in 4 mL of in thionyl chloride and heated to reflux for 2.5 hours. The excess thionyl chloride is removed from the reaction mixture under reduced pressure and the resulting crude residue (2.6 g) is used without any further purification.

IR (KBr, cm$^{-1}$): 1732.3, 1700, 1533.3, 1478.1, 1212.9, 826.6.

Starting from this compound compounds according to general formulas I and II wherein R$^1$ is a linear or branched C$_{1-4}$-alkyl group can be prepared reacting this compound with the appropriate alkyl alcohol.

(b) N-piperidinyl-5-(4-chlorophenyl)-1-(2,4-dichlorophenyl)-4,5-dihydropyrazole-3-carboxamide

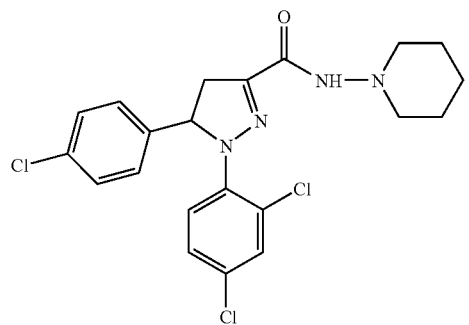

Under nitrogen atmosphere N-aminopiperidine (0.6 mL, 5.6 mmoles) and triethylamine (4 mL) were dissolved in methylene chloride (25 mL). The resulting mixture was ice-cooled down to 0° C. and a solution of 5-(4-chlorophenyl)-1-(2,4-dichlorophenyl)-4,5-dihydro-pyrazole-3-carboxylic acid chloride obtained in step (c) in methylene chloride (15 mL) was added dropwise. The resulting reaction mixture was stirred at room temperature (approximately 25° C.) overnight. Afterwards the reaction mixture was washed with water, followed by a saturated aqueous solution of sodium bicarbonate, then again with water, dried over sodium sulfate, filtered and evaporated to dryness in a rotavapor. The resulting crude solid was crystallized from ethanol. The crystallized solid was removed via filtration and the mother liquors were concentrated to yield a second fraction of crystallized product. The two fractions were combined to give a total amount of 1.7 g (57% of theoretical yield) of N-piperidinyl-5-(4-chlorophenyl)-1-(2,4-dichlorophenyl)-4,5-dihydropyrazole-3-carboxamide having a melting point of 183-186° C.

IR (KBr, cm$^{-1}$): 3222.9, 2934.9, 1647.4, 1474.7, 1268.3, 815.6.

$^1$H NMR (CDCl$_3$, δ): 1.4 (m, 2H), 1.7 (m, 4H), 2.8 (m, 4H), 3.3 (dd, J=6.1 y 18.3 Hz, 1H), 3.7 (dd, J=12.5 and 18.3 Hz, 1H), 5.7 (dd, J=6.1 and 12.5 Hz, 1H), 7.0-7.2 (m, 6H), 7.4 (s, 1H).

The compounds according to the following examples 2-6 have been prepared analogously to the process described in Example 1 in combination with Example 0.

Example 2

5-(4-Chloro-phenyl)-1-(2,4-dichloro-phenyl)-4,5-dihydro-1H-pyrazole-3-carboxylic acid-[1,2,4]triazol-4-yl amide Melting point: 134-138° C.
IR (KBr, cm$^{-1}$): 3448, 1686, 1477, 1243, 1091, 821.
$^1$H NMR (CDCl$_3$, δ): 3.1 (dd, J=6.2 and 17.9 Hz, 1H), 3.7 (dd, J=12.3 and 17.9 Hz, 1H), 5.9 (dd, J=6.2 and 12.3 Hz, 1H), 7.2-7.5 (m, 7H), 8.7 (s, 2H), 12.0 (bs, 1H).

Example 3

5-(4-Chloro-phenyl)-1-(2,4-dichloro-phenyl)-4,5-dihydro-1H-pyrazole-3-carboxylic acid-(4-methyl-piperazin-1-yl)-amide hydrochloride Melting point: 150-155° C.
IR (KBr, cm$^{-1}$): 3433, 1685, 1477, 1296, 1246, 1088, 1014, 825.
$^1$H NMR (CDCl$_3$, δ): 2.7 (d, J=4.2 Hz, 3H), 3.0-3.4 (m, 9H), 3.6 (dd, J=11.9 and 17.9 Hz, 1H), 5.8 (dd, J=5.5 and 11.9 Hz, 1H), 7.1 (d, J=8.4 Hz, 2H), 7.25 (2d, J=8.4 and 8.7 Hz, 3H), 7.4 (d, J=2.2 Hz, 1H), 7.5 (d, J=8.7 Hz, 1H), 9.8 (s, 1H), 11.2 (bs).

Example 4

5-(4-Chloro-phenyl)-1-(2,4-dichloro-phenyl)-4,5-dihydro-1H-pyrazole-3-carboxylic acid diethylamide This compound was obtained in form of an oil.
IR (film, cm$^{-1}$): 2974, 1621, 1471, 1274, 1092, 820.
$^1$H NMR (CDCl$_3$, δ): 1.2 (m, 6H), 3.3-3.9 (m, 6H), 5.6 (dd, J=5.8 and 11.7 Hz, 1H), 7-7.25 (m, 7H).

Example 5

[5-(4-Chloro-phenyl)-1-(2,4-dichloro-phenyl)-4,5-dihydro-1H-pyrazol-3-yl]-piperidin-1-yl-methanone Melting point: 105-110° C.
IR (KBr, cm$^{-1}$): 2934, 1622, 1470, 1446, 1266, 1010, 817.
$^1$H NMR (CDCl$_3$, δ): 1.7 (m, 6H), 3.4 (dd, J=5.7 and 17.9 Hz, 1H), 3.7 (m, 3H), 3.9 (m, 2H), 5.6 (dd, J=6.1 y 11.9 Hz, 1H), 7-7.25 (m, 7H).

Example 6

N-[5-(4-Chloro-phenyl)-1-(2,4-dichloro-phenyl)-4,5-dihydro-1H-pyrazole-3-carbonyl]-4-methyl-phenyl-sulfonamide This compound was obtained in form of an amorph solid.
IR (KBr, cm$^{-1}$): 1697, 1481, 1436, 1340, 1169, 1074, 853.

$^1$H NMR (CDCl$_3$, δ): 2.4 (s, 3H), 3.2 (dd, J=6.6 and 18.3 Hz, 1H), 3.6 (dd, J=12.8 and 18.3 Hz, 1H), 5.8 (dd, J=6.6 and 12.8 Hz, 1H), 7 (d, J=8.2 Hz, 2H), 7.2 (s, 1H), 7.3-7.4 (m, 6H), 8 (d, J=8.1 Hz, 2H), 9 (s, 1H).

Example 7

N-oxide of N-piperidinyl-5-(4-chlorophenyl)-1-(2,4-dichlorophenyl)-4,5-dihydropyrazole-3-carboxamide Under nitrogen gas as an inert atmosphere N-piperidinyl-5-(4-chlorophenyl)-1-(2,4-dichlorophenyl)-4,5-dihydropyrazole-3-carboxamide (0.15 g, 332 mmoles) was dissolved in 7 ml of dichloromethane. The resulting solution was ice-cooled to 0° C. and m-chloroperbenzoic acid (0.204 g, 0.83 mmoles) added in several portions. After stirring for 15 minutes a control via thin layer chromatography showed that no starting material was remaining. A saturated solution of sodium bicarbonate was then slowly added, the organic phase separated, washed with water, dried over sodium sulfate and filtered. The filtered solution was evaporated to dryness and the crude product was purified via column chromatography yielding 78 mg (50% of theoretical yield) of the N-oxide of N-piperidinyl-5-(4-chlorophenyl)-1-(2,4-dichlorophenyl)-4, 5-dihydropyrazole-3-carboxamide in form of a white solid having a melting point of 115-120° C.

IR (KBr, cm$^{-1}$): 3202, 1678, 1654, 1474, 1309, 1107.
$^1$H-NMR (CDCl$_3$, δ): 1.6 (m, 2H), 1.8-2.0 (m, 4H), 2.55 (m, 2H), 3.3 (dd, J=6.3 Hz and 18.2 Hz, 1H), 3.7 (m, 3H), 5.8 (dd, J=6.3 Hz and 12.5 Hz, 1H), 7.0-7.3 (m, 7H), 8.5 (s, 1H.)

Pharmacological Data/Testing:

The compound according to example 0 is an inhibitor of high blood levels of triglicerides. This effect has been probed in obese mice fed with high fat diet. In the following paragraphs it is described the method and the results obtained in this study.

I. In-Vivo Testing for Regulation of Triglycerides in Blood Plasma

The study was done using six weeks old male mice B6 Lep ob/ob, obtained from Charles River (France). Mice were divided in 3 groups: I (control), II (vehicle), III (example 0).

Group I:
The animals of the group I received the standard diet (D-12450B, Research Diets, NJ, USA).

Group II:
The animals of the groups II and III were fed with a High Fat Diet (D-12492, Research Diets, NJ, USA), in both cases for 7 weeks (References 1 and 2).

Group II:
The animals of the groups III were fed with a High Fat Diet (D-12492, Research Diets, NJ, USA), in both cases for 7 weeks (References 1 and 2).

At the end of the feeding period of 7 weeks, it was started the treatment period (14 days): Group II mice received the vehicle (10 ml/kg/day, po, of the aqueous solution of acacia gum, 5% WN). Group III was administered with 30 mg/kg/day, po, of the inventive compound 5-(4-chlorophenyl)-1-(2, 4-dichlorophenyl)-4,5-dihydro-pyrazole-3-carboxylic acid according to Example 0. Group I didn't received any treatment. The three groups of mice had the same diet than in the previous period.

At the end of the 14 days period of treatment, the blood levels of triglicerides of the animals were determined.

The analysis of the whole blood samples was done using test strips "Lipid panel" and the photometric Analyzer Cardio-Check Test System, from PA Instruments Polymer Technology Systems Indianapolis, Ind.-46268, USA (Distributed in Spain by Novalab Iberica S.A.L, Madrid, Spain).

The results obtained were the following:

| Group | Diet | Treatment | Triglicerides, whole blood levels (mg/dl) | Relative levels |
|---|---|---|---|---|
| I | Standard | — | 61 | 100% |
| II | High Fat | Vehicle 10 ml/kg/day po | 122.4 (*) | 200.6% |
| III | High Fat | Example 0 30 mg/kg/day po | 67.5 (N.S.) | 110.6% |

(*): $p < 0.05$, Anova followed Bonferroni t-test, compared with Group I.
(NS): Not significant diference, compared with Group I.

The results showed that Group II mice receiving high fat diet had significantly higher trigliceridies blood levels than the control Group I. But the administration of the compound according to Example 0 (Group II) improved the trigliceridies blood levels, which were not different of the levels of the group I, which received standard diet.

FIG. 1 shows the clear reduction of triglyceride levels in blood plasma. The level (Group II) returns to the control level of Group I compared to the clearly raised levels found in the Group II without the treatment with the compound according to Example 0.

Thus, it has been proved the inhibitory effect of the inventive compound 5-(4-chlorophenyl)-1-(2,4-dichlorophenyl)-4,5-dihydro-pyrazole-3-carboxylic acid according to Example 0 on the high blood levels of triglicerides.

REFERENCES

1.—Lambert P. D. et al. "Cyliary neurotrophic factor activates leptin-like pathways and reduces body fat"
P.N.A.S. 2001, 28 (8): 4652-4657
2.—Grasa M. M. et al "Oleoyl-Estrone Iowens the body weight of both ob/ob and db/db mice.
Hozm. Metab. Res 2000, 32: 246-250

II. In-Vivo Testing for Regulation of Triglycerides in Blood Plasma

In a second set of experiments carried out similar to the tests shown above the TG (triglyceride) levels of diet-induced obese mice in blood were determined.

Mice receiving a high fat diet were—after a feeding period of 6 days—either treated p.o. with vehicle (0.5% HPMC) or with the compound according to example 0 (30 mg/kg/day p.o.).

TG levels in blood were determined on day 28 after beginning of the treatment.

TG (triglyceride) levels were 1.28±25 mmoles/l in the group treated with vehicle and only 0.80±0.07 mmoles/l in the group treated with the inventive compound 5-(4-chlorophenyl)-1-(2,4-dichlorophenyl)-4,5-dihydro-pyrazole-3-carboxylic acid according to Example 0. The results were statistically highly significant with an ANOVA factorial, Fisher's post-hoc test of *** $p<0.005$ vs. vehicle.

Thus, again the inhibitory effect of the inventive compound 5-(4-chlorophenyl)-1-(2,4-dichlorophenyl)-4,5-dihydro-pyrazole-3-carboxylic acid according to Example 0 on the high blood levels of triglicerides was demonstrated.

The invention claimed is:
1. Substituted pyrazoline compounds of formula I,

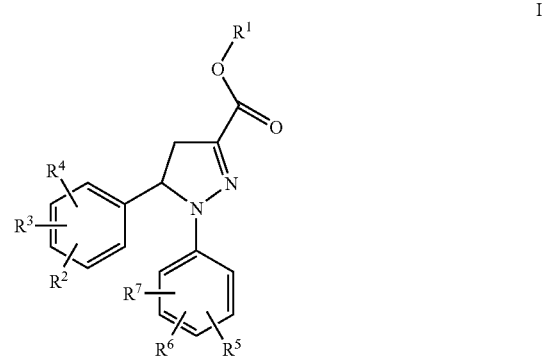

wherein
$R^1$ represents hydrogen or a linear or branched $C_{1-4}$-alkyl group,
$R^2$, $R^3$ and $R^4$ independently of each other represent hydrogen, a linear or branched $C_{1-6}$-alkyl group, a linear or branched $C_{1-6}$-alkoxy group, a halogen atom, $CH_2F$, $CHF_2$, $CF_3$, CN, OH, $NO_2$, —(C=O)—$R^8$, SH, $SR^8$, $SOR^8$, $SO_2R^8$, $NH_2$, $NHR^8$, $NR^8R^9$, —(C=O)—$NH_2$, —(C=O)—$NHR^8$ or —(C=O)—$NR^8R^9$ whereby $R^8$ and $R^9$ for each substituent independently represent linear or branched $C_{1-6}$ alkyl,
$R^5$ and $R^6$ independently of each other represent a linear or branched $C_{1-6}$-alkoxy group, a halogen atom, $CH_2F$, $CHF_2$, $CF_3$, CN, OH, $NO_2$, —(C=O)—$R^{10}$, SH, $SR^{10}$, $SOR^{10}$, $NH_2$, $NHR^{10}$, $NR^{10}R^{11}$, —(C=O)—$NH_2$, —(C=O)—$NHR^{10}$ or —(C=O)—$NR^{10}R^{11}$, whereby $R^{10}$ and optionally $R^{11}$ for each substituent independently represent linear or branched $C_{1-6}$ alkyl;
$R^7$ represents hydrogen, a linear or branched $C_{1-6}$-alkyl group, a linear or branched $C_{1-6}$-alkoxy group, a halogen atom, $CH_2F$, $CHF_2$, $CF_3$, CN, OH, $NO_2$, —(C=O)—$R^{10}$, SH, $SR^{10}$, $SOR^{10}$, $NH_2$, $NHR^{10}$, $NR^{10}R^{11}$—(C=O)—$NH_2$, —(C=O)$NHR^{10}$ or —(C=O)—$NR^{10}R^{11}$, whereby $R^{10}$ and optionally $R^{11}$ for each substituent independently represent linear or branched $C_{1-6}$ alkyl;
with the proviso that
if $R^1$ and $R^7$ are H and $R^5$ and $R^6$ both represent Cl in the 3- and 4-position of the phenyl ring neither of $R^2$, $R^3$ and $R^4$ may represent F in the 4-position of the phenyl ring if the other two of $R^2$, $R^3$ and $R^4$ both represent H;
optionally in a form of one of its stereoisomers or a racemate or in a form of a mixture of at least two of its stereoisomers, in any mixing ratio, or a corresponding N-oxide thereof, or a physiologically acceptable salt thereof.

2. Compounds according to claim 1, characterized in that at least one of $R^2$, $R^3$ or $R^4$ represents hydrogen, while at least one of $R^2$, $R^3$ or $R^4$ is different from hydrogen.

3. Compounds according to claim 1, characterized in that $R^7$ represents hydrogen.

4. Compounds according to claim 1, characterized in that $R^2$, $R^3$ and $R^4$ independently of each other represent hydrogen, a linear or branched $C_{1-6}$-alkyl group, a halogen atom, or $CF_3$.

5. Compounds according to claim 1, characterized in that $R^5$ and $R^6$ independently of each other represent, a halogen atom, or $CF_3$.

6. Compounds according to claim 1, characterized in that R² represents a chlorine atom in the 4-position of the phenyl ring, while R³ and R⁴ represent hydrogen.

7. Compounds according to claim 1, characterized in that R⁵ and R⁶ each represent chlorine atoms in the 2- and 4-position of the phenyl ring, while R⁷ represents hydrogen.

8. Compounds according to claim 1, characterized in that R¹ represents hydrogen, methyl or ethyl.

9. Compounds of formula II according to claim 1

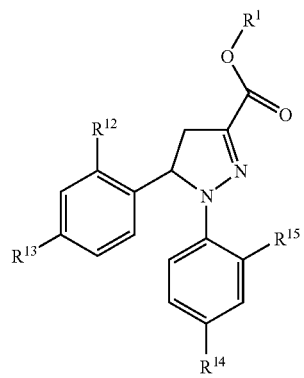

II wherein
R¹ represents hydrogen or a linear or branched $C_{1-4}$-alkyl group,
R¹² or R¹³ independently of each other represent a linear or branched $C_{1-6}$-alkyl group, a linear or branched $C_{1-6}$-alkoxy group, a halogen atom, $CH_2F$, $CHF_2$, $CF_3$, CN, OH, $NO_2$, SH, $NH_2$, hydrogen, methyl, ethyl, F, Cl, Br or $CF_3$,
R¹⁴ or R¹⁵ independently of each other represent a linear or branched $C_{1-6}$-alkoxy group, a halogen atom, $CH_2F$, $CHF_2$, $CF_3$, CN, OH, $NO_2$, SH, $NH_2$, methyl, ethyl, F, Cl, Br or $CF_3$,
optionally in a form of one of its stereoisomers or a racemate or in a form of a mixture of at least two of its stereoisomers, in any mixing ratio, or a corresponding N-oxide thereof, or a physiologically acceptable salt thereof.

10. Compounds according to claim 9 characterized in that R¹² and R¹³ independently of each other represent hydrogen, a linear or branched $C_{1-6}$-alkyl group, a halogen atom, or $CF_3$.

11. Compounds according to claim 9, characterized in that R¹⁴ and R¹⁵ independently of each other represent a halogen atom, or $CF_3$.

12. Compounds according to claim 9, characterized in that R¹³ represents Cl and R¹² represents hydrogen.

13. Compounds according to claim 9, characterized in that R¹⁴ and R¹⁵ each represent Cl.

14. Compounds according to claim 9, characterized in that R¹ represents hydrogen, methyl or ethyl.

15. A compound according to claim 1 which is:
5-(4-chloro-phenyl)-1-(2,4-dichlorophenyl)-4,5-dihydro-1H-pyrazol-3-carboxylic acid, optionally in the form of a corresponding N-oxide, a corresponding salt.

16. Process for the manufacture of substituted pyrazoline compounds of formula I or II wherein R¹ is hydrogen, according to claim 1, characterized in that at least one benzaldehyde compound of formula III

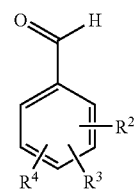

(III)

wherein R², R³ and R⁴ have the meaning according to claim 1, is reacted with a pyruvate compound of formula (IV)

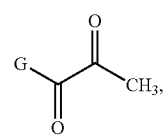

(IV)

wherein G represents an OR group with R being a branched or unbranched $C_{1-6}$ alkyl radical or G represents an O'K group with K being a cation, to yield a compound of formula (V)

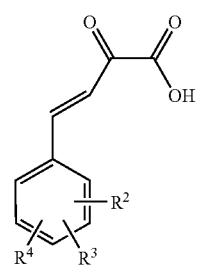

(V)

which is optionally isolated or optionally purified, and which is reacted with an optionally substituted phenyl hydrazine of formula (VI)

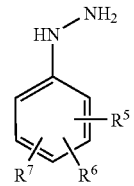

(VI)

or a corresponding salt thereof, wherein R⁵, R⁶ and R⁷ have the meaning according to claim 1, under inert atmosphere, to yield a compound of formula (VII)

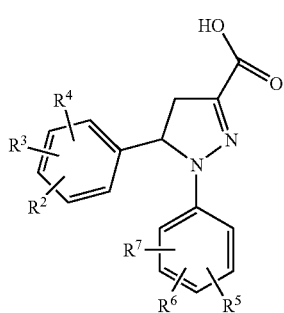
(VII)

wherein $R^2$, $R^3$, $R^4$, $R^5$, $R^6$ and $R^7$ have the meaning as given above, which is optionally isolated or optionally purified, and optionally esterified to an alkyl-ester if in the substituted pyrazoline compound of formula I according to claim 1 $R^1$ is a linear or branched $C_{1-4}$-alkyl group.

17. Composition comprising at least one substituted pyrazoline compound of formula I or II according to claim 1, and optionally one or more pharmaceutically acceptable excipients.

* * * * *